United States Patent [19]

Prestele

[11] Patent Number: 4,559,831
[45] Date of Patent: Dec. 24, 1985

[54] METHOD AND DEVICE FOR FLOW MEASUREMENT OF SMALL LIQUID VOLUMES

[75] Inventor: Karl Prestele, Erlangen, Fed. Rep. of Germany

[73] Assignee: Siemens Aktiengesellschaft, Berlin and Munich, Fed. Rep. of Germany

[21] Appl. No.: 647,568

[22] Filed: Sep. 6, 1984

[30] Foreign Application Priority Data

Sep. 26, 1983 [DE] Fed. Rep. of Germany ....... 3334805

[51] Int. Cl.$^4$ ............................................. G01F 1/708
[52] U.S. Cl. ............................... 73/861.05; 73/861.08
[58] Field of Search ........... 73/861.05, 861.06, 861.08; 324/71.1, 71.4; 340/606, 609; 128/DIG. 12, DIG. 13; 604/67

[56] References Cited

U.S. PATENT DOCUMENTS

| | | | |
|---|---|---|---|
| 1,616,481 | 2/1927 | Allen | 73/861.05 |
| 2,683,986 | 7/1954 | Bartlett et al. | |
| 3,500,366 | 3/1970 | Chesney | 324/714 |
| 3,621,715 | 11/1971 | Soederkvist et al. | |
| 3,739,636 | 6/1973 | Versaci et al. | |
| 3,898,637 | 8/1975 | Wolstenholme | 128/DIG. 13 |

FOREIGN PATENT DOCUMENTS

| | | |
|---|---|---|
| 861610 | 7/1949 | Fed. Rep. of Germany . |
| 2218459 | 1/1973 | Fed. Rep. of Germany . |
| 2752328 | 6/1978 | Fed. Rep. of Germany . |
| 2135304 | 12/1972 | France . |
| 2083612 | 3/1982 | United Kingdom . |

Primary Examiner—Herbert Goldstein
Attorney, Agent, or Firm—Mark H. Jay

[57] ABSTRACT

The invention relates to a method and a device for flow measurements of small liquid volumes through a thin tube. The measurement of small liquid volumes on the order of e.g. 1–500 μl/h is important, especially for medication dispensers. Gas bubbles are fed into the tube, the diameter of the gas bubbles being essentially the same size as the inside diameter of the tube. The liquid flow pushes the gas bubble forward. The flow time of the gas bubble is determined at pre-set measuring points which are located at a predetermined distance from each other along the tube. A control signal may be emitted according to the flow time and may be used to control the flow rate. The method and the device are suitable for electrically conductive liquids, in which variations in the electrical resistance is determined in the direction of the flow when the bubbles enter the measuring section.

14 Claims, 3 Drawing Figures

METHOD AND DEVICE FOR FLOW MEASUREMENT OF SMALL LIQUID VOLUMES

BACKGROUND OF THE INVENTION

The invention relates to a method for flow measurement of small liquid volumes passing through a tube-like element, in which a gas bubble is introduced, whose flow time in the longitudinal direction of the tube-like element is measured between two predetermined points located at a distance from each other, the diameter of the gas bubble being selected to be approximately the same as the inside diameter of the tube-like element, and the flow rate being calculated from the flow time. The invention also relates to a flow rate measurement device for the application of the method.

The problem of measuring very small liquid flow volumes, especially between 1 and 500 $\mu l/h$ is difficult, particularly for medication dispensers. Therefore, a satisfactory functional control has not been possible for miniaturized devices. However, since patients can be endangered if functional problems in such devices are not identified, such as control is urgently needed. Operational problems can occur in the dispensing device itself, as by breakdowns of the structural elements or battery deficiencies, and also in the dosage path, due to blockage by drug floccules of the narrow feeding hose or tube, or to deposits on the drug discharge opening. The need for a reliable functional control is even greater in the case of implantable medication despensers.

A method and a device of the aforementioned type are described in U.S. Pat. No. 3,739,636. This shows a method for measuring flow rates, in which two detectors are spaced a predetermined distance from each other. A needle or a three-way stopcock connected with a gas reservoir is used to feed a gas bubble, which enters the tube-like element and is carried along by the flow current. As the gas bubble passes by the first detector, the timing begins. As soon as it reaches the second detector, the timing ends. A lamp, on the one hand, and a photocell, on the other, are used as detectors. This arrangement has the disadvantage that where the flow measurement apparatus must be of the smallest possible size, for example, in medical applications such as medication dispensers, a lamp and a photocell are too bulky and are therefore unsuitable. Similar methods and devices are also described in British patent publication No. 2,083,612 and in U.S. Pat. No. 3,621,715.

DE-PS 831 610 also deals with the measurement of small volumes of liquid. In this reference, a gas bubble is fed into a gauge tube to measure fuel consumption in a motor vehicle. The procedure is repeated at regular intervals. For measurement purposes, two shutoff valves separate the gauge tube from the liquid flow. A scale is used to determine how far the gas bubble travels inside the tube. This reference states that electrical contacts located face-to-face inside the tube can be used as gas bubble detectors. For any variation in the resistance of the circuit in which the contacts and a power source are located, a relay closes. This arrangement is disadvantageous because it requires a complicated manual procedure for evaluating the flow rate, and this is not practical for a medication dispenser. Furthermore, measurement requires an indicator scale which cannot be used in an implantable medication dispenser.

DE-OS No. 27 52 328 is also related to fuel consumption measurement. Here, ions are generated by an ionising first electrode. The ions are carried with the fuel flow and are recaptured at a second electrode located downstream. The flow time is calculated from the travel time of the ions between the two electrodes. This device is stated to be especially suitable for measuring high flow rates, because it relies on longitudinal displacement of the ions, i.e., displacement in the direction of the flow. During low flow rates or small liquid flows, the ions would again recombine, and a false measuring signal would result.

DE-OS No. 22 18 459 describes a method for measuring liquid flow in a hydraulic system. In particular, it deals with the measurement of the mass flow of a discontinuous phase or of the flow volume of a liquid mixture containing a conductive fluid. The electric conductivity is measured with two electrodes which are in contact with the liquid flow. This measurement produces a signal indicating a change in conductivity which is the result of a change in the component ratio of the liquid mixture. The mass flow is calculated for the flow time from the measured conductivity changes. A prerequisite for the measurement is that the changes in conductivity take place at a high speed. They therefore trace back to turbulence. High flow rates are a prerequisite in this measurement method also. In contrast, the invention herein relates to the measurement and detection of small amounts of liquid and low flow rates in a tube-like element with a small cross-section.

One object of the present invention is to provide a method and a device which are especially suitable for the detection of very small volumes of liquid flow, particularly for medication dispensers, where few and small structural elements are desirable.

SUMMARY OF THE INVENTION

This task is accomplished in that for the flow measurement of an electrically conductive liquid, the electrical resistance between two points situated in the longitudinal direction of the tube-like element is determined. There is a relatively low resistance between the two points when there is no gas bubble between them, and a relatively high resistance when a gas bubble is present.

An arrangement for the application of this method consists of a flow measuring device with a tube-like element through which a liquid flows, a means for repeated feeding of a gas bubble into the tube-like element, and another means for determining the passage of the gas bubble between two predetermined points on the tube-like element. According to the invention, an electrode is provided at each one of the two points on the tube-like element, and a means for measuring variations in the electrical resistance is connected between the two electrodes.

One advantage of the subject method and subject device resides in its usability for small liquid volumes through narrow tube-like elements such as hoses or rigid tubes in a medication dispenser. Because of the electrical measuring procedure, bulky structural elements such as a lamp and a photocell are eliminated. At the same time, measurement of the electrical conductivity along a defined path of the tube means that only two electrodes and their corresponding feed wires are required.

The conductive liquid in motion may be thin or viscous.

A further embodiment relating to the design of the device affords an additional important advantage. In the case of conductive liquids it is unnecessary to differentiate over a larger bandwidth of tightly grouped resistance values, but only between two states, "conductive" and "non-conductive". A gas bubble which is present in the liquid between the two points cuts off the conductivity. This leads to a high reliability in the result obtained. With only two possible states, errors in measurements and in interpretations of measurements are rare.

Another important advantage exists when the device is used in a medication dispenser; in this case the metal housing of the device forms a test point, i.e., a test electrode. The housing is connected electrically to the catheter tip of the dispenser. The liquid can be monitored as it discharges from the catheter end. With the aid of the electrical resistance-measurement device it is further possible to identify variations in the electrical resistance on the catheter tip directly. Such variations may be caused, for example, by blockage of the catheter tip or by deposits of body tissue on the catheter tip. Problems of this type can be identified by placing the measuring electrode near the housing. Preventive steps, such as replacing the catheter tip, can be taken in time.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 1:
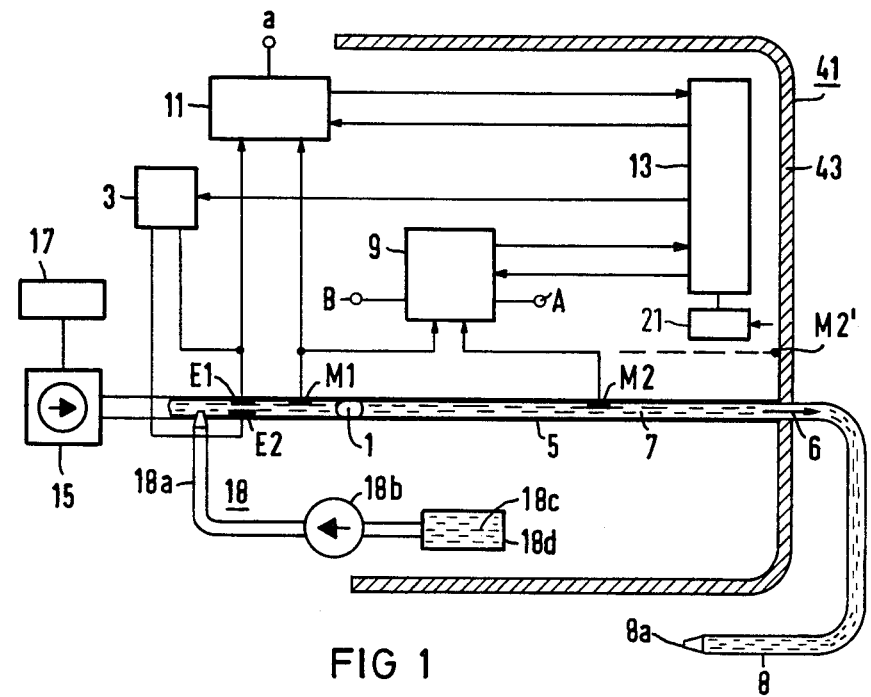
FIG. 1 is a schematic block diagram of a preferred embodiment of the invention.

In FIG. 1 E1 and E2 are two electrodes for repeated production of a single gas bubble 1. These electrodes E1 and E2 are electrically connected to a circuit 3 for generating bubbles through electrolysis, and are located along a hollow element 5 which here is a tube (for example, a hose) through which a liquid 7 flows in the direction shown by arrow 6. Electrodes E1, E2 face each other inside tube 5 and thus electrically contact liquid 7. These electrodes E1, E2 may be metallic pins driven through the wall of tube 5 or, as illustrated, metal platelets connected to electrical wires. As required electrodes E1 and E2 are supplied with DC voltage by means of circuit 3. Tube 5 in particular may be part of a catheter 8 (not shown) with discharge opening 8a of an implantable dispenser through which liquid medication is pumped to an application point in a patient (not shown).

A measuring section is located downstream from electrodes E1 and E2. At the beginning of this section a first electrode M1 is located, and at the end, a second electrode M2. By these electrodes, M1, M2, two spaced-apart points are established along tube 5. In this case also, electrodes M1, M2 are so located that they remain in constant electrical contact with liquid 7. To measure the electrical conductivity between these electrodes M1, M2, they are connected through electrical wires to circuit 9. This circuit 9 and the electrodes M1, M2 form an electrical arrangement which detects the passage of a gas bubble 1. Circuit 9 need not be highly sensitive in measuring resistance. It suffices if circuit 9 can differentiate between "conductive" and the "non-conductive" states. Circuit 9 need only detect a substantial change in the electrical resistance. The length of the measuring section between the two electrodes, M1, M2, depends on the expected flow speed, the type of liquid 7 and the inside diameter of tube 5.

The electrolytic electrode E1 and the first test electrode M1 are also connected to an interference bubble recognition circuit 11, which determines, by means of resistance measurement or conductivity measurement whether or not a gas bubble is present between the electrodes E1 and M1. Such a bubble may be a gas bubble 1 generated by the electrolytic electrodes E1, E2, or an interfering gas bubble. The distance between electrodes E1 and M1 may be smaller than between electrodes M1, M2. Alternatively, electrodes E1 and M1 may be combined into one electrode. E2 would then be located across from this combined electrode.

Consequently, circuit 11 for identifying interfering gas bubbles can emit an alarm signal a. The signal is further fed to an alarm device (not shown), which emits an audio or video alarm when interfering gas bubbles occur.

A control circuit 13 takes over the checking from circuits 11 and 9 to determine if there is conductivity between electrodes E1 and M1, on the one hand, and M1 and M2, on the other. Depending on the answer obtained, circuit 13 initiates further steps which will be described later. Tube 5 is connected to a pump 15, possibly through a catheter (not shown). Pump 15 feeds liquid 7 from a reservoir 17 through tube 5. At the end of tube 5 liquid 7 is ready for further use. This liquid may be, for example, an insulin solution, fed in measured doses into the body (not shown) of the patient.

In the case of the embodiment shown in FIG. 1 it is important that the diameter of the generated gas bubble 1 not be smaller than, but rather be equal to, the inner diameter of tube 5. As a result, liquid 7 will not be able to flow past the gas bubble 1, but will push the bubble ahead of it. For volume flows of about 1 to 500 μl/h, (such as are here considered, the inside diameter of the tube being on the order of 0.1 to 2.0 mm) it can be assumed that no turbulence or other flow irregularities occur. Therefore, the flow process can be considered uniform (laminar).

In light of the low flow volumes involved, feeding or injecting gas bubble 1 is not difficult. No flushing takes place before the desired diameter of gas bubble 1 is attained. To obtain a gas bubble 1 of sufficient size, it is advisable for the electrode E1 (on which gas bubble 1 forms) to have a special shape. For example, an elongated electrode affords sufficient surface so that the gap between electrodes E1 and E2 is not insulated before the necessary bubble size develops. Specially curved electrodes which would also contribute to the shape of the gas bubble 1 may also be used.

As already mentioned, gas bubble 1 can be generated by electrolysis. For example, if liquid 7 contains water, it can be decomposed into hydrogen ($H_2$) and oxygen ($O_2$) if the voltage of electrodes E1 and E2 is sufficiently high. For a liquid 7 which cannot be electrolyzed, gas bubble 1 can be produced under controlled conditions from a device 18 by means of a hose or tube 18a which discharges into the tube 5. The hose or tube 18a is supplied with gas 18c from a gas supply reservoir 18d by means of a pump 18b.

Figure 2:
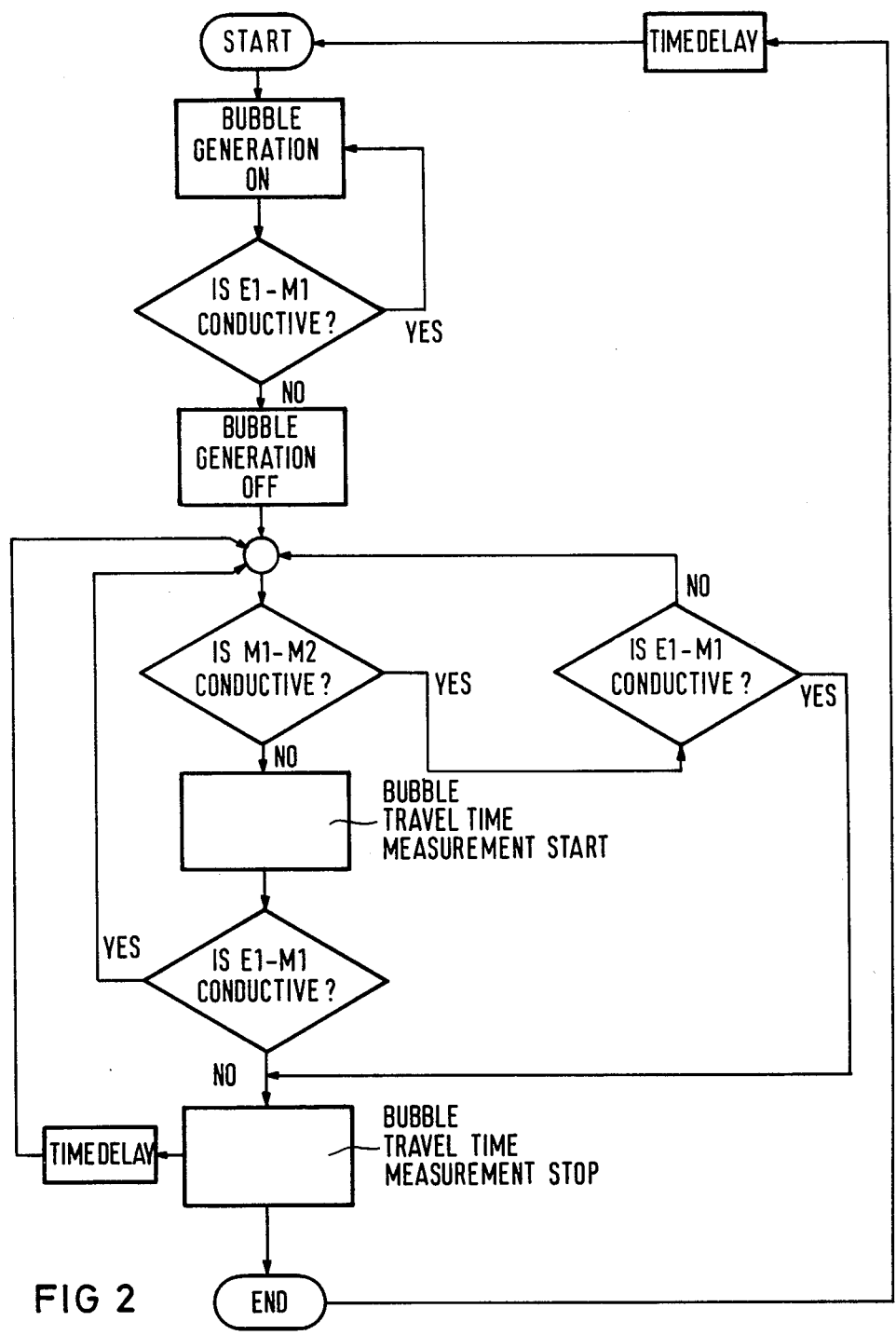
FIG. 2 is a flow chart of the measuring method carried out by the embodiment of FIG. 1.

According to FIG. 2, a typical measurement sequence with the device shown in FIG. 1 is as follow:

Control circuit 13 sends a start signal to circuit 3 for bubble generation. In this exemplary embodiment an electrolytic device applies a DC voltage to electrodes E1 and E2. Small gas bubbles are formed on at least one of the electrodes, for example, electrode E1. These small bubbles combine into a larger gas bubble 1 which fills the diameter of tube 5, after a certain period, and moves in the direction of arrow 6, or remains in the area of electrodes E1, E2 if the liquid is at a standstill. As a result, electrode E1 is electrically insulated from electrode M1. Control circuit 13 checks at predetermined intervals whether the section located between electrodes E1 and M1 is "conductive" or "non-conductive". If it is "conductive", gas bubble 1 is not sufficiently large to fill the diameter of tube 5, and gas bubble generation circuit 3 remains on. If the section is "non-conductive", control circuit 13 sends a stop signal to circuit 3, thus switching it off.

After this operation is completed, control circuit 13 checks at intervals the measuring section between electrodes M1 and M2 to determine whether it is "conductive" or "non-conductive". If section M1–M2 is "conductive" (relatively low resistance), section E1–M1 will be checked and tested for conductivity to determine whether gas bubble 1 is still ahead of measuring section M1–M2. If this is the case, control circuit 13 will again check section M1–M2 for "non-conductivity". This checking cycle is repeated until the gas bubble 1 generated has entered measuring section M1–M2. As soon as the corresponding checking is positive, and the measuring section M1–M2 is "non-conductive" (relatively high resistance), the control circuit 13 triggers the flow measurement. Circuit 9 (FIG. 1) contains an arrangement for the measurement of the flow. The circuit 9 emits an output signal A which measures the passage time of gas bubble 1 along measuring section M1–M2 and thereby measures the flow rate.

Interfering bubbles may possibly be fed from pump 15, for example, due to a blockage in the discharge conduit or because reservoir 17 is empty. To determine whether such interfering bubbles enter the measuring section M1–M2, control device 13 checks section E1–M1 for conductivity at predetermined intervals.

(a) If section E1–M1 is non-conductive, an interfering bubble must have entered it. In this case, the continuity of the measurement is interrupted by control circuit 13 and reset to zero. At the same time, the interfering bubble is treated as if it were a generated gas bubble 1. Control circuit 13 switches back to signal "stop bubble generation". This immediately follows the flow time interruption and zero reset.

(b) However, if section E1–M1 remains conductive, i.e., if no interfering bubble has entered it, testing will determine if gas bubble 1 is still in the measuring section M1–M2. Control circuit 13 switches back again to "stop bubble generation", without prior interruption of the measurement as in case 1.

This cycle continues until the measuring section M1–M2 as well as section E1–M1 are "conductive". The flow time measurement is then stopped by control circuit 13 and the result fed as an output signal A for further use. This further use may result, for example, in a change of the speed of pump 15. Output signal A may also trigger an audio and/or video alarm. The further use can be a conversion to flow rate and the indication thereof, which can be carried out, e.g., through an inductive signal coupling or radio signal in an implanted device.

In a further embodiment of the method, the interfering bubbles can be recorded as they are detected; and, starting from a set frequency or from a limit value of the volume percentage of gas bubbles 1 in liquid 7, a signal B can trigger a video and/or audio alarm.

When the flow time stops, the measuring process is completed and control circuit 13 can be reset to its starting point by means of an adjustable timing element 21. Circuit 13 will again emit a starting signal to circuit 3 to begin another generation of a bubble.

It is advantageous for tube 5 to have measuring sections M1–M2, E1–M1 made of a non-flexible material which is resistant to deformation. This assures a constant volume inside measuring sections M1–M2 and E1–M1.

In a further embodiment of the invention all components are mounted in one housing 41. This is particularly appropriate for implantable devices. Therefore, it may be advantageous to monitor a larger portion of the dispenser path in particular, to monitor whether the flow of liquid 7 at the discharge opening 89 is satisfactory.

This can be done if test electrode M2 is connected to the housing wall 43, so that the housing wall 43 becomes electrically conductive. This is indicated by dotted lines, and as test electrode M2'. The entire path from the discharge opening 89 to test electrode M1 is then checked by conductivity measurement to see if gas bubble 1 is present. The electrical resistance of the fabric extending from the housing wall 43 to discharge opening 8a for liquid 7 can be neglected in comparison to the electrical resistance of gas bubble 1 in tube 5.

Figure 3:
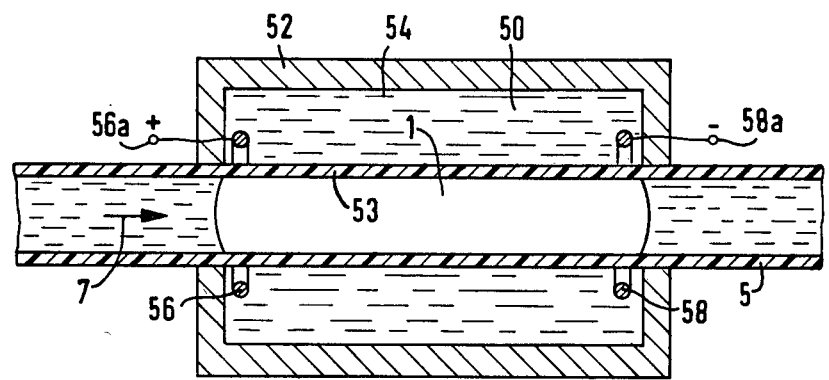
FIG. 3 a longitudinal section in a tube-like element with a separate electrolytic chamber for generation of bubbles.

FIG. 3 shows a longitudinal section through tube 5, which in this case has a separate electrolytic chamber 50 for generating gas bubbles 1. Electrolytic chamber 50 is cylindrical and positioned centrally around tube 5. Electrolytic chamber 50 is bounded by sheath 52. The inside of electrolytic chamber 50 is bounded by segment 53 of tube 5. The chamber 50 is filled with an electrolyte 54, e.g., NaOH. This electrolyte 54, which is contained in the electrolytic chamber 50, can therefore be considered to be a reservoir of gas. Two annular electrodes 56,58 are located inside electrolytic chamber 50 concentrically around tube 5. Electrodes 56, 58 are connected by electrical connections 56a or 58a to a source of DC voltage. These connections from electrolyte chamber 50 lead to the outside.

Tube segment 53 is a gas-permeable wall. It may be formed, e.g., of silicon rubber, and separates the interior of tube 5 from electrolytic chamber 50. In the illustrated example, tube 5 consists entirely of a silicon rubber hose. An intermediate piece may be installed as a gas permeable wall in the area of electrolytic chamber 50.

A DC voltage is applied to electrodes 56, 58, so that gas is formed in electrolytic chamber 50. The gas penetrates by diffusion through permeable section 53 into tube-like element 5. There it develops into gas bubble 1.

One advantage of this embodiment is that liquid 7 need not be electrolytic and that it is not affected by the electrolytic process. Electrolyte 54 and the material of electrodes 56 and 58 should be so coordinated that efficient gas bubble formation is possible.

Those skilled in the art will understand that changes can be made in the preferred embodiments here described, and that these embodiments can be used for other purposes. Such changes and uses are within the scope of the invention, which is limited only by the claims which follow.

What is claimed is:

1. A method for measuring small liquid flow volumes passing through a tube-like conduit in which a gas bubble is introduced, the longitudinal flow time of the bubble being measured between two points on the conduit which are separated from each other by a predetermined distance, the diameter of the bubble being approximately equal to the inside diameter of the conduit and the flow rate being determinable from the flow time, comprising the steps of:

measuring the electrical resistance between the two points on the conduit;

characterizing the resistance as a one of two categories which include a relatively low resistance corresponding to an absence of a gas bubble between the two points and a relatively high resistance corresponding to a presence of a gas bubble between the two points;

starting a timing period upon measuring a relatively high resistance between the two points; and stopping the timing period upon measuring a relatively low resistance between the two points.

2. The method of claim 1, further comprising the steps of checking the conduit to detect gas bubbles which interfere with liquid flow, and repeating flow measurement upon such detection.

3. The method of claim 2, wherein ongoing measurement of flow time is cut off upon such detection and a moment of such detection is used as a new beginning for a new measurement of flow time.

4. The method of claim 1, further comprising the steps of deriving a control signal from the measured flow time, and using the control signal to regulate the liquid flow rate.

5. A flow measurement device of the type having a conduit through which a liquid flows, means for repeatedly feeding a gas bubble into the conduit and a means for timing the passage of the gas bubble between two points along the conduit which are separated from each other by a predetermined distance, comprising:

first and second electrodes, each located at a corresponding one of the two points along the conduit;

means for measuring electrical resistance between the first and second electrodes; and means for activating and deactivating said timing means in accordance with changes in electrical resistance measured between the first and second electrodes.

6. The device of claim 5, wherein said means for measuring resistance distinguishes only between a conductive state and a non-conductive state.

7. The device of claim 5 wherein said means for repeatedly feeding gas bubbles contains an electrolytic device which generates gas bubbles by electrolysis.

8. The device of claim 5, wherein the conduit is set in an electrically conductive housing, wherein a discharge opening of the conduit is outside the housing in an electrically conductive environment; and wherein the housing is one of said electrodes.

9. The device of claim 5, further comprising means for detecting interfering gas bubbles in the conduit.

10. The device of claim 9, wherein said means for detecting interfering gas bubbles comprises means for the measurement of resistance and two electrodes spaced apart from each other along the conduit and being connected to said means for the measurement of resistance.

11. The device of claim 9, wherein said means for detecting interfering gas bubbles includes means for emitting an alarm signal.

12. The device of claim 5, wherein said means for timing is connected to regulate the flow rate of the liquid.

13. The device of claim 5, wherein said means for repeatedly feeding gas bubbles is an electrolytic decomposition device which contains an electrolyte located outside the conduit.

14. The device of claim 13, wherein the electrolyte surrounds a gas-permeable part of the conduit, whereby gas which is generated during electrolysis may enter the liquid.

* * * * *